Figure 1:
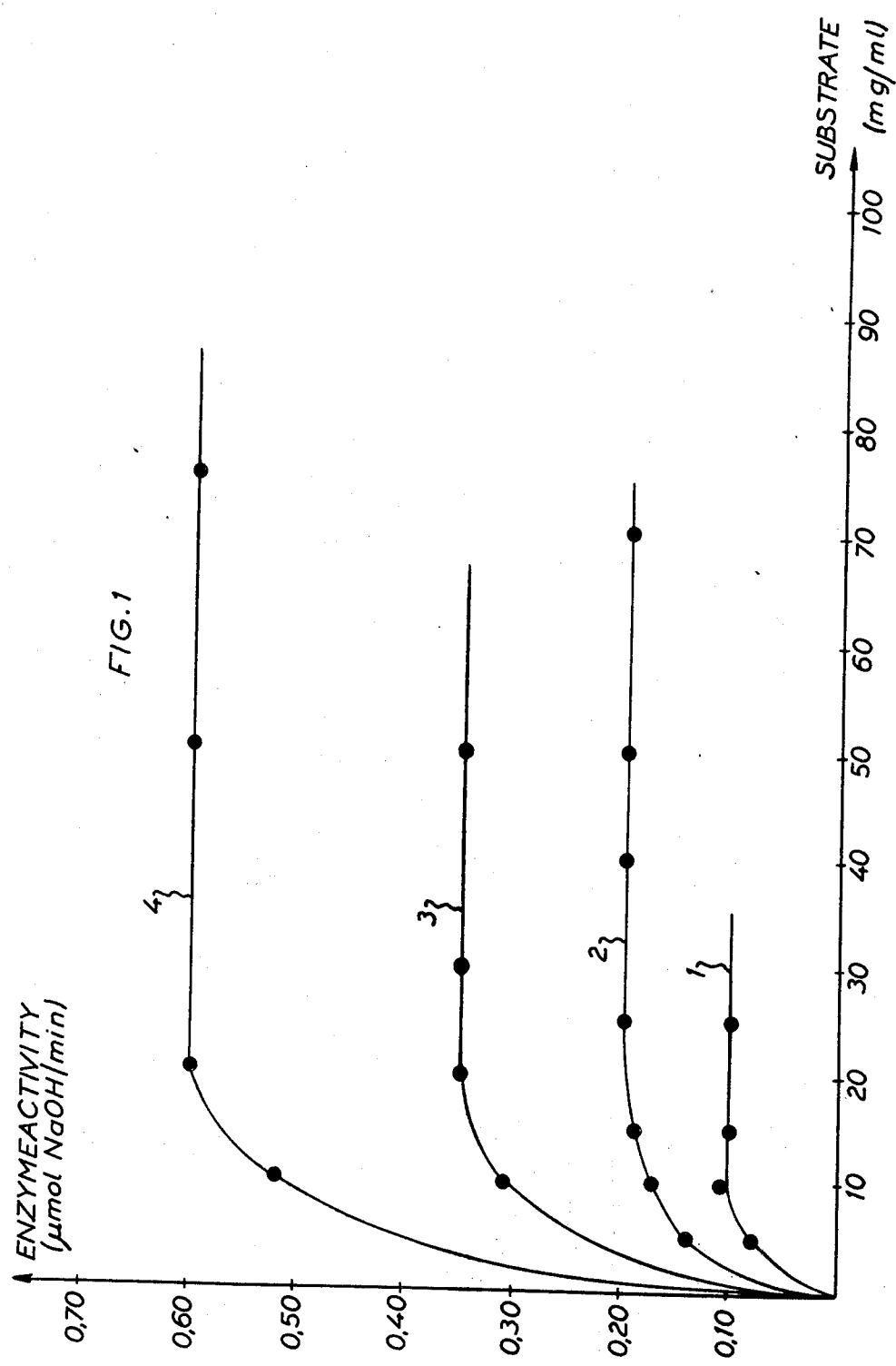

United States Patent [19]

Agerhem et al.

[11] 4,284,719

[45] Aug. 18, 1981

[54] SUBSTRATE COMPOSITION AND USE THEREOF

[75] Inventors: Halina Agerhem, Malmö; Hans J. Nilsson, Lund, both of Sweden

[73] Assignee: Kockums Chemical AB, Malmö, Sweden

[21] Appl. No.: 143,065

[22] Filed: Apr. 23, 1980

[30] Foreign Application Priority Data

May 17, 1979 [SE] Sweden ................................ 7904320

[51] Int. Cl.³ .......................... C12Q 1/34; C12Q 1/00; C12M 1/40
[52] U.S. Cl. ...................................... 435/18; 252/408; 435/4; 435/288
[58] Field of Search ..................... 252/408; 422/56, 57; 435/4, 18, 180, 181, 182, 287, 288, 299

[56] References Cited

U.S. PATENT DOCUMENTS

| | | | |
|---|---|---|---|
| 2,671,028 | 3/1954 | Clark | 435/805 X |
| 3,647,713 | 3/1972 | Morse | 252/408 |
| 3,806,417 | 4/1974 | Beaucamp et al. | 252/408 X |
| 3,822,189 | 7/1974 | Tornmarck | 435/4 X |
| 4,043,871 | 8/1977 | Blixt et al. | 435/805 X |
| 4,219,334 | 8/1980 | Schluter et al. | 435/4 X |

*Primary Examiner*—Robert J. Warden
*Attorney, Agent, or Firm*—Beveridge, DeGrandi et al.

[57] ABSTRACT

A substrate composition for reaction with an enzyme, comprising carrier particles and a substrate adsorbed thereto and being characterized in that the carrier consists of polyvinylchloride. Polyvinylchloride of emulsion type is particularly preferred. A preferred substrate is tricaproin which is enzymatically split by lipase enzyme. The use of the substrate composition as a substrate component in enzymatic time-temperature indicating devices is also disclosed.

15 Claims, 2 Drawing Figures

SUBSTRATE COMPOSITION AND USE THEREOF

The present invention relates to a substrate composition for reaction with an enzyme, which composition contains a water-insoluble hydrophobic substrate and a particulate carrier for the substrate. The invention also relates to the use of such a substrate composition in an enzymatic time-temperature indicating device.

In the context of this application, a substrate is by definition a substance acted upon by an enzyme or ferment.

Enzymatic reactions, i.e. a reaction between a substrate and an enzyme, are made use of within widely different technical fields. Normally, both the substrate and the enzyme are in the form of an aqueous solution. Over the last years, great efforts have been made to improve the enzyme side. To this end, the enzyme has been bound to a carrier so as to increase enzyme stability, handleability and permit re-use. Relatively insignificant efforts have however been made to elaborate the substrate side, despite the fact that great problems arise when the substrate is in the form of, for instance, a water-insoluble substance, such as a water-immiscible liquid. Thus, for the determination of lipases, use is made of for instance olive oil or various synthetic triglycerides in the form of water-immiscible oily liquids. In order to effect lipase analysis, it is general practice to emulsify the oily substrate in water with the aid of surfactants and other emulsion stabilizers. In order to make the analysis reproducible, the emulsification of the substrate is performed under standardized conditions. None the less, the use of emulsions entails considerable drawbacks. Thus, is is practically impossible to obtain a uniform droplet size in the emulsion, which results in an undefined surface of the substrate with ensuing poor reproducibility for the enzymatic reaction. Furthermore, the emulsions cannot be stored over very long periods but are unstable, particularly at low temperatures. On account of these drawbacks, it has been difficult to study enzymatic activity to an acceptable degree of accuracy and reproducibility, for instance in enzyme analysis. Another particular field where these drawbacks are evident, is the case of enzymatic time-temperature indicating devices which are adapted to control the handling of sensitive products, such as frozen or refrigerated food, vaccines, blood products, medicines, photographic film etc. The fundamental construction of such time-temperature indicating devices is disclosed in U.S. Pat. No. 2,671,028. The difficulty in this connexion is int. al. that the indicating device is subjected to temperatures below freezing point and so, it is quite impossible to use a liquid substrate in the form of an emulsion, since the emulsion will be broken on account of the low temperature.

In order to overcome the above drawbacks, it has been suggested in U.S. Pat. No. 4,043,871 to bring both liquid and solid water-insoluble substrates to solid powder form by a combination with a particulate carrier. The carrier is characterized in that it has a large specific surface area of more than 50 $m^2/g$, particularly indicated preferred carrier materials being inorganic carriers of silica type, such as silica aerogel of a surface area of over 200 $m^2/g$. The substrate is adsorbed to the carrier and by the combination of substrate and carrier with large surface area there are obtained increased enzymatic activity and reproducibility as compared with previously used substrate emulsions as at the same time the above-mentioned drawbacks of substrate emulsions, such as instability, are substantially reduced.

However, the present invention has proved capable of affording still further advantages if, instead of the preferred inorganic carrier of silica type according to the above U.S. patent specification, use is made of an organic polymer, and in particular polyvinyl chloride, as carrier. Consequently, substrate saturation is here gained, i.e. maximum and constant enzyme activity in the reaction with an enzyme, even at a very low substrate concentration which is considerably lower than what is possible according to prior art technique. This implies a great and surprising improvement, which will be readily appreciated by anyone skilled in the art.

According to the invention, the particular features of which will appear from the claims, there is thus provided a pulverulent substrate composition for reaction with an enzyme, which composition, besides optional additives, such as tenside, comprises a water-insoluble hydrophobic substrate adsorbed on a particulate carrier, the invention being characterized in that the carrier is polyvinyl chloride free of plasticizer and is of an average grain size of at most 0.5 mm, and that the substrate makes up 1–30% by weight of the composition.

Preferably, the composition also comprises 0.1–3 and, most preferably, 1–2% by weight of tenside.

Other optional additives which may be used, e.g. to dilute the substrate phase or modify its melting point, are such compounds as: (a) have a solubility of less than 0.1% by weight in water at 20° C., (b) are miscible with the organic substrate phase, (c) have a lower melting point than the substrate, (d) have a boiling point at least as high as the substrate, and (e) do not act as an inhibitor to the enzyme of the substrate.

According to one aspect of the invention, the substrate composition is used as substrate component in a time-temperature-integrating indicating device of enzymatic type.

Another aspect of the invention comprises an aqueous suspension for use in an enzymatic reaction, said suspension comprising (a) a water phase, and (b) the aforesaid pulverulent substrate composition of the invention suspended in said water phase.

A further aspect of the invention is directed to an enzymatic time-temperature-integrating indicating device comprising two compartments separated by a rupturable partition, wherein one compartment contains the aforesaid aqueous suspension and the other compartment contains an enzyme for said substrate, and at least one of the compartments includes a pH indicator.

Still another aspect of the invention is directed to said indicating device when in activated form, that is when the partition has been ruptured. In this instance, the enzymatic time-temperature-integrating indicating device comprises a compartment which contains an aqueous solution including an enzyme and a pH indicator, said aqueous solution having suspended therein the pulverulent substrate composition of the invention.

A further aspect is directed to an enzymatic time-temperature-integrating device comprising a compartment which contains an aqueous solution including an enzyme and a pH indicator, said aqueous solution having suspended therein the pulverent substrate composition of this invention.

The invention also relates to a method of enzymatic reaction, comprising providing an aqueous solution including an enzyme and a pH indicator, combining said aqueous solution with a composition comprising the pulverulent substrate composition of the invention, reacting said enzyme with said substrate, and determining a change in colour of said solution by a change of pH.

Another aspect of the invention relates to a method of determining the activity of an enzyme, comprising providing an aqueous solution including the enzyme and adding to said solution a predetermined amount of the pulverulent substrate composition of claim 1, reacting the enzyme with the substrate while generating an enzymatic reaction product, the determination of the enzymatic activity being based on the amount of reaction product produced per time unit.

Still another aspect of the invention concerns a method of determining the activity of an enzyme, comprising providing an aqueous solution including the enzyme and adding to said solution a predetermined amount of the pulverulent substrate composition of the invention, agitating said mixture and maintaining the pH of said mixture constant by the addition of a base or an acid, and determining the activity of the enzyme as the added amount per time unit of said base or acid.

The carrier of the invention has an average grain size of up to 0.5 mm, because carrier grains of a size above 0.5 mm are difficult to suspend stably. There is no critical lower limit for the size of the carrier grains, but a practical lower limit may be set at about 0.5 $\mu$m, since smaller grains are difficult to produce.

Moreover, the carrier should have a glass transition temperature (Tg) of more than about 80° C. in order that the carrier when used should always maintain its discrete particle form and not soften and fuse with the substrate.

A further requirement is that the carrier be inert to the enzymatic system, i.e. it should not exert any negative influence on either the substrate, the enzyme or the product which is formed in the enzymatic reaction. The carrier should also be inert to the solvents used when coating the substrate on the carrier, such that it does not soften or dissolve therein.

Finally, the carrier should have a certain porosity to be capable of adsorbing and retaining the substrate. The porosity of the carrier is a function of its surface. It is difficult to set any strict limits to the porosity of the carrier, but in principle it may be stated that a porosity corresponding to a surface of less than about 25 m$^2$/g is preferred and that a porosity corresponding to about 5–10 m$^2$/g is the most preferred.

The above general criteria are satisifed extremely well by polyvinyl chloride (PVC).

A particularly preferred PVC carrier consists of PVC prepared by emulsion polymerization, which is referred to herein as emulsion type PVC. This PVC type has an average grain size within the indicated range, from 0.5 $\mu$m to 0.5 mm, but the grains consist of agglomerates of smaller primary particles of an average size of about 0.1–1 $\mu$m, normally about 0.2–0.6 $\mu$m.

Even if emulsion type PVC is particularly preferred in the invention, other types of PVC, such as PVC prepared by bulk polymerization and PVC prepared by suspension polymerization, are by no means excluded. Generally speaking, all types of PVC can be used according to the invention. Furthermore, the PVC carrier material of the invention should be as pure as possible, i.e. free of plasticizer and other conventional additives, in order to avoid affecting the enzymatic system. The PVC often has a certain minor tenside content of about 1–2% by weight which emanates from the manufacture of the PVC. In order to avoid possible disturbing influence from such tenside, the carrier material is washed in the event it contains a tenside, so as to remove the tenside before the carrier material is used in the invention.

As is evident from the above, the present invention is restricted to liquid and solid substrates which are hydrophobic and insoluble in water. By "insoluble in water" is meant that the substrate has a solubility of less than 0.1% by weight in water at 25° C. The reason for this is that water-soluble substrates are released from the carrier in aqueous medium whereas hydrophilic water-insoluble substrates are poorly bound to the PVC carrier.

Substrates particularly comprised by the invention are water-insoluble esters.

Among such esters, triglycerides are preferred in particular, which depending on the length and degree of saturation of the carbon chain in the included fatty acid moiety are liquids or solids. In order to satisfy the requirement that the substrate be insoluble in water, the fatty acid moiety in saturated fatty acids should have at least 4 carbon atoms, which corresponds to a water solubility of less than 0.01% by weight. Consequently, triacetin and tripropionin are not substrates in keeping with the invention, whereas tributyrin is satisfactory. A preferred substrate of triglyceride type is tricaproin (glyceryl tricapronate) which undergoes enzymatic reaction with lipase enzymes. As examples of other preferred substrates of the triglyceride type may be mentioned: tributyrin, tricaprylin, triolein and olive oil.

Among other preferred substrates of the ester type, mention may be made of diglycerides, such as 1,3-dicaproin and 1,3-diolein; monoglycerides, such as 1-monoolein or 1-monostearin; sorbitan esters, such as sorbitan monooleate and sorbitan monostearate; cholesterol esters, such as cholesterol acetate and cholesterol hexanoate; methyl, ethyl and propyl esters of ethylene tetracarboxylic acid, adipic acid and 2,4-dioxo valerianic acid.

As examples of water-insoluble substrates which do not belong to the group of esters, may be mentioned stereoids, such as cholesterol, cortisol and prednisolone.

As compared with previously used substrate carriers, and above all the above-mentioned silica carriers, the PVC carrier according to the present invention has several substantial advantages, as will be described in greater detail hereinbelow.

The PVC carrier according to the invention is neutral, i.e. it does not affect the pH value, and it does not seem to have any effect on the enzymatic reaction or the resulting reaction product. Furthermore, the PVC carrier is hydrophobic, which is a great advantage in hydrophobic substrates of for instance triglyceride type, since the substrate is easily adsorbed to the carrier and remains fixedly anchored thereto. The hydrophobic interaction between the carrier and the substrate ensures a solid anchorage of the substrate to the carrier. By this solid anchorage, the substrate composition will be very stable, both in the dry state, when stored and in aqueous medium, and no spontaneous release of the substrate from the carrier will take place. A most considerable advantage of the substrate composition with PVC carrier according to the invention is that the substrate, despite its solid anchorage to the carrier, is very readily accessible for enzymatic reaction. If experiments are carried out with constant enzyme concentration, but with increasing substrate concentration, it will be found that a constant maximum reaction rate will be attained even at a very low substrate concentration. This may be explained by the fact that the substrate coated on a carrier will offer to the enzyme molecules a much larger accessible substrate surface than the corresponding amount of substrate without a carrier, for instance in the form of an emulsion. In the case of hydrophobic water-insoluble substrates, it is in fact the substrate accessible to the enzyme at the interface (between aqueous phase and substrate phase) which constitutes the "effective" substrate concentration (see H. Brockerhoff and R. G. Jensen, Lipolytic Enzymes, Academic Press, New York (1974)).

Even when compared with the substrate composition according to the previously discussed U.S. Pat. No. 4,043,871, the composition according to the invention attains substrate saturation at a substantially lower substrate content. This is unexpected and surprising in regard of the relation intimated above between substrate saturation and accessible substrate surface, for the carrier of the above U.S. patent specification has a surface area of at least 50 $m^2/g$ and normally at least 200 $m^2/g$, whereas the carrier of the present invention has a surface which preferably is less than 25 $m^2/g$ and which normally is only 5–10 $m^2/g$. Thus, it is evident that a large surface area of the carrier does not automatically give a large accessible substrate surface.

One consequence of the fact that maximum reaction rate is attained even at very low substrate concentrations is that it will not be necessary to use high substrate contents in the substrate composition of the invention, which is favourable, since the substrate is the expensive component whereas the PVC carrier is the cheap one. Generally, the substrate content of the substrate carrier composition of the invention is about 1–30% by weight, calculated on the total composition. 1% by weight of substrate here is a practical lower limit, since lower contents will give a too low enzymatic reaction rate. Apart from economic and other practical considerations, the upper limit of 30% by weight is also determined by the fact that substrate contents exceeding 30% by weight will not give a completely dry product. A substantially dry free-flowing powder is important to facilitate grinding and size separation of particles and to make it possible to substantially uniformly distribute the powder in the liquid system in which it is used. According to the invention, a preferred content range for the substrate is 5–25% by weight, calculated on the total composition.

Different methods for preparing the substrate composition according to the invention will be described hereinbelow.

More precisely, the preparation is effected by adding the substrate to a solvent or a solvent mixture which has high dissolving capacity with respect to the substrate but which does not dissolve the carrier. Suitable solvents of this type may easily be selected by anyone skilled in the art and as examples hereof may be mentioned lower alcohols, such as methanol and ethanol. To the solution is preferably also added 0.1–3% by weight of tenside, calculated on the final composition, in order to improve the dispersibility of the substrate composition in aqueous medium. The desired amount of the pulverulent PVC carrier is then added and the mixture is vaporized, preferably at reduced pressure and moderately raised temperature, under agitation, for instance in a rotary flask evaporator. When all of the solvent has been driven off, the finished product is removed and ground and, if desired, sieved to a powder of desired grain size.

Another mode of preparation is to pour the carrier powder into a dry-mixing apparatus with a high speed agitator and add, under agitation, a fine jet of liquid substrate. By the vigorous agitation in the mixer, the substrate will be distributed on the carrier grains and a substrate composition uniformly coated on the carrier grains will be obtained.

It should be pointed out that, although the above-mentioned methods of preparation are the most preferred at present, it is of course possible to prepare the substrate composition of the invention by other methods. Thus, according to an alternative, less preferred method, a solution of substrate is prepared in a solvent, a PVC carrier is added and the mixture is successively dispensed into an aqueous body, the substrate precipitating as a coating on the carrier grains.

In principle, the substrate composition of the present invention is usable for all purposes which include reaction between substrate and enzyme. Particular fields where the invention may be used to advantage are enzyme analysis and standardization, qualitative and quantitative enzyme determination in clinical chemistry, and as substrate component in the previously mentioned enzymatic time-temperature indicating devices.

The large accessible surface of the substrate composition of the invention entails optimum conditions for the determination of small amounts of enzyme. Further, in that the PVC carrier has a defined surface, the substrate will also have a defined surface, this making the enzymatic reaction reproducible. These properties make it possible when using the substrate composition of the invention, both qualitatively and quantitatively to determine small amounts of enzyme, which is valuable in medical diagnostics, since the appearance of small amounts of enzymes or variation in the enzyme concentration in for instance blood often is an indication of a state of illness. The present invention thus has made it possible, at an early stage, to make a reliable diagnosis of different states of ill-health.

An important aspect of the invention is its use in enzymatic time-temperature indicating devices. One embodiment of such an indicating device comprises two small closed plastic ampoules which are separated by a common rupturable partition. One plastic ampoule contains an aqueous solution of enzyme, while the other plastic ampoule contains a substrate suspended in an aqueous medium. To permit indicating the reaction product generated by the enzymatic reaction when the indicating device is activated, one of the plastic ampoules, preferably the one containing the substrate, includes a pH indicator. When the indicating device is activated, i.e. when the time-temperature indication is to start, the rupturable partition is broken in that a compressing force is exerted on one of the plastic ampoules. The contents of the plastic ampoules will thus communicate with each other such that the contents of the ampoules are mixed and an enzymatic reaction is initiated. The enzymatic reaction proceeds with the formation of a reaction product, such as caproic acid, if the substrate is tricaproin and the enzyme is a lipase, in dependence upon temperature and time. The pH indicator present is intended, by colour change, to indicate the exceeding of a certain amount of reaction product, such as acid. The difficulties to provide a reliable enzymatic time-temperature indicating device are most considerable. For instance, one must be able to manipulate the enzymatic reaction in a reliable and reproducible manner. These difficulties are greatly increased in that the enzyme and substrate amounts used must be kept small, considering the size and cost of the indicating device. In that, as previously mentioned, the reaction rate of the substrate composition of the invention, even at very small substrate concentrations, is dependent only on enzyme concentration and not on substrate concentration, one of the major obstacles to providing a time-temperature indicating device with satisfactory reproducible function is eliminated. The other above-indicated advantages of the substrate composition of the invention are also, of course, of avail in this connection.

To facilitate understanding of the invention, a few illustrating Examples thereof will be given below.

EXAMPLE 1

Preparation of PVC carrier coated with tricaproin substrate.

100 g of emulsion PVC (Pevikon® PE 712 from Kema Nord, Sweden; particle size: 0.2% >63 μm), washed with ethanol, was slowly poured under agitation into a solution consisting of 20 g of tricaproin (TC) and 300 ml of ethanol which had been preheated to 60° C., in a 2 liter evaporation flask. After complete suspension of the polyvinyl chloride, the flask was connected to an evaporator (Rotovapor, Büchi Laboratorium-Technik AG, Flawil, Switzerland). Temperature was maintained at 60° C. with the aid of a water bath and the ethanol was driven off during 60 min at reduced pressure (about 20 mm Hg, water jet pump). The resulting product was a dry and odourless powder consisting of aggregates of different sizes. The aggregates were very brittle and after grinding in a mill (Alpine-Augsburg, Federal Republic of Germany), there was obtained a powder with a particle size distribution similar to that of the starting material. In order to remove aggregates of relatively larger size, the powder was sieved through a screen having a mesh of 70 μm.

EXAMPLE 2

Example 1 was repeated, with the difference, however, that 2 g of tenside (BRIJ® 72 Atlas Chemical Industries, Inc. Wilmington, Del., USA) was added to the ethanol solution before coating.

EXAMPLE 3

Preparation of PVC carrier coated with tributyrin substrate.

Example 1 was repeated, with the difference, however, that tricaproin was replaced by 20 g of tributyrin (TB).

EXAMPLE 4

Preparation of PVC carrier coated with triacetin substrate.

Example 1 was repeated, with the difference, however, that tricaproin was replaced by 20 g of triacetin (TA).

EXAMPLE 5

Preparation of PVC carrier coated with tripropionin substrate.

Example 1 was repeated, with the difference, however, that tricaproin was replaced by 20 g of tripropionin (TP).

EXAMPLE 6

Preparation of PVC carrier coated with olive oil substrate.

Example 1 was repeated, with the difference, however, that tricaproin was replaced by 20 g of olive oil and ethanol was replaced by a mixture consisting of 80% of ethanol and 20% of chloroform.

EXAMPLE 7

Example 6 was repeated, with the difference, however, that 2 g of tenside (Brij 72) was added to the ethanol-chloroform solution before coating.

EXAMPLE 8

Preparation of PVC carrier coated with triolein substrate.

Example 6 was repeated, with the difference, however, that olive oil was replaced by 20 g of triolein.

EXAMPLE 9

The substrate properties of the substrate compositions according to Examples 1–8 were studied with the aid of pancreatic lipase in a pH-stat apparatus at 25° C. The theoretical method is described in Marchis-Mouren et al (1959), Arch Biochem Biophys, Vol. 83, pp 309–319. The measurements were performed under nitrogen-gas atmosphere and vigorous agitation. 9 ml of 0.1 M aqueous solution of sodium chloride was placed in a thermostatted vessel, whereupon a weighed amount of substrate composition was added. pH was adjusted to 8.0 and 1 ml of an enzyme solution was added. The enzyme solution had the following composition.

| | |
|---|---|
| glycerol | 45% by volume |
| albumin | 1 mg/ml |
| calcium chloride | 10 mM |
| pancreatic lipase, | (0.04–1.2 μg/ml) |

The consumption of 0.02 M sodium hydroxide required to maintain pH at 8.0 was automatically displayed on a recorder. Enzyme activity, measured as μmol consumed sodium hydroxide/min, was calculated from the resulting printer diagram which showed a linear consumption of sodium hydroxide during the time the measurement was performed. A deviation from linear consumption would have shown either increasing or decreasing enzyme reaction.

The result of measurements with the tricaproin preparation according to Example 2 appears from Table 1 and FIG. 1.

The result of measurements with the tributyrin preparation according to Example 3 appears from Table 2.

As is shown in Tables 1 and 2, maximum and constant enzyme activity (substrate saturation) was obtained upon addition of a certain, very small amount of substrate composition. A further increase of the substrate amount did not increase enzyme activity. The substrate concentration at which substrate saturation occurs, is dependent upon the enzyme concentration. The higher the enzyme concentration is, the higher substrate concentration is required for obtaining substrate saturation.

TABLE 1

| Enzyme concentration (μg/ml) (curve no. in FIG. 1) | Enzyme activity (μmol NaOH/min) Amount of substrate composition (mg/ml) | | | | | | | | | |
|---|---|---|---|---|---|---|---|---|---|---|
| | 5 | 10 | 15 | 20 | 25 | 30 | 40 | 50 | 70 | 75 |
| 0.04 (curve 1) | 0.08 | 0.11 | 0.10 | — | 0.10 | — | — | — | — | — |
| 0.10 (curve 2) | 0.14 | 0.17 | 0.19 | — | 0.20 | — | 0.20 | 0.20 | 0.20 | — |
| 0.20 (curve 3) | — | 0.31 | — | 0.35 | — | 0.35 | — | 0.35 | — | — |
| 0.40 (curve 4) | — | 0.52 | — | 0.60 | — | — | — | 0.60 | — | 0.60 |

TABLE 2

| Enzyme concentration (μg/ml) | Enzyme activity (μmol NaOH/min) Amount of substrate composition (mg/ml) | | | | |
|---|---|---|---|---|---|
| | 5 | 10 | 20 | 35 | 50 |
| 0.10 | 0.29 | 0.38 | 0.39 | 0.37 | 0.39 |

TABLE 3

| Substrate form | Enzyme activity (μmol NaOH/min) Amount of TC (mg/ml) | | | | | | |
|---|---|---|---|---|---|---|---|
| | 2.5 | 5.0 | 10.0 | 15.0 | 20.0 | 30.0 | 40.0 |
| Emulsified TC | — | 0.08 | 0.13 | — | 0.16 | 0.18 | 0.21 |
| Example 2 | 0.50 | 0.59 | 0.60 | 0.60 | 0.60 | — | — |

TABLE 4

| Substrate form | Enzyme activity (μmol NaOH/min) Amount of substrate composition (mg/ml) | | | | | | |
|---|---|---|---|---|---|---|---|
| | 5 | 10 | 25 | 50 | 75 | 100 | 200 |
| Emulsified olive oil | — | 0.20 | 0.28 | 0.33 | 0.38 | 0.46 | 0.60 |
| Example 6 | 0.20 | 0.32 | 0.46 | 0.50 | 0.60 | 0.60 | — |
| Example 7 | 0.12 | 0.32 | 0.66 | 0.64 | 0.60 | — | — |
| Example 8 | — | — | — | 0.47 | — | 0.54 | 0.54 |

EXAMPLE 10

In this example, the substrate composition of Example 2 (with PVC carrier) was compared with free emulsified TC (i.e. without carrier) by the method indicated in Example 9. Table 3 shows the measured enzyme activities for different concentrations of TC, either in the free state or coated on a carrier, at an enzyme concentration of 0.4 μg/ml. This experiment discloses a particular advantage of the substrate composition according to the invention, i.e. that substrate saturation is obtained even at very low substrate concentration.

EXAMPLE 11

In this example, the substrate composition according to Examples 6-8 (with PVC carrier) was compared with free emulsified olive oil (i.e. without carrier), by using the method of Example 9. Table 4 shows the measured enzyme activities for different substrate concentrations at an enzyme concentration of 0.4 μg/ml. It appears from Table 4 that substrate saturation is obtained in the invention even at very low substrate concentration.

EXAMPLE 12

The reproducibility of the coating method was studied with the aid of three different coatings realized according to Example 2 by the pH-stat method of Example 9. In this instance, the substrate concentration was 100 mg/ml and the enzyme concentration was varied between 0.1 and 1.2 μg/ml. The high reproducibility between the three different coatings will appear from Table 5.

TABLE 5

| Enzyme concentration (μg/ml) | Enzyme activity (μmol NaOH/min) | | |
|---|---|---|---|
| | Coating 1 | Coating 2 | Coating 3 |
| 0.10 | 0.26 | 0.29 | 0.27 |
| 0.40 | 0.64 | 0.64 | 0.64 |
| 0.80 | 1.10 | 1.12 | 1.14 |
| 1.00 | 1.39 | 1.40 | 1.37 |
| 1.20 | 1.56 | 1.62 | 1.64 |

EXAMPLE 13

In this example, the bond between the carrier and different triglycerides was examined. The following triglycerides were studied: Triacetin (TA), Tripropionin (TP), Tributyrin (TB), and Tricaproin (TC). Coating was carried out as appears from Examples 1, 3, 4, 5.

The different substrate samples were divided each into two portions. The first portion of each substrate sample was used to determine the original enzyme activity by the pH-stat method of Example 9. In each case, the amount of substrate composition was 100 mg/ml and enzyme concentration was 1.0 μg/ml, except for tributyrin, where a lower enzyme concentration (0.4 μg/ml) was used.

The second portion (2 g) of each substrate sample was washed for 3 h with large excess of distilled water in order to remove soluble substrate, if any. The substrate samples were then dried and examined with respect to enzyme activity as above.

Table 6 shows the enzyme activity before and after washing for removal of soluble substrate. As appears from Table 6, the water solubility of triacetin and tripropionin makes these substances loosen from the hydrophobic carrier and pass to aqueous phase.

TABLE 6

| Substrate | Enzyme activity before washing (μmol NaOH/min) | Enzyme activity after washing (μmol NaOH/min) |
|---|---|---|
| TC | 2.24 | 2.30 |
| TB | 1.50 | 1.50 |
| TP | 1.74 | 0.28 |
| TA | 0.14 | 0.00 |

EXAMPLE 14

Figure 2:
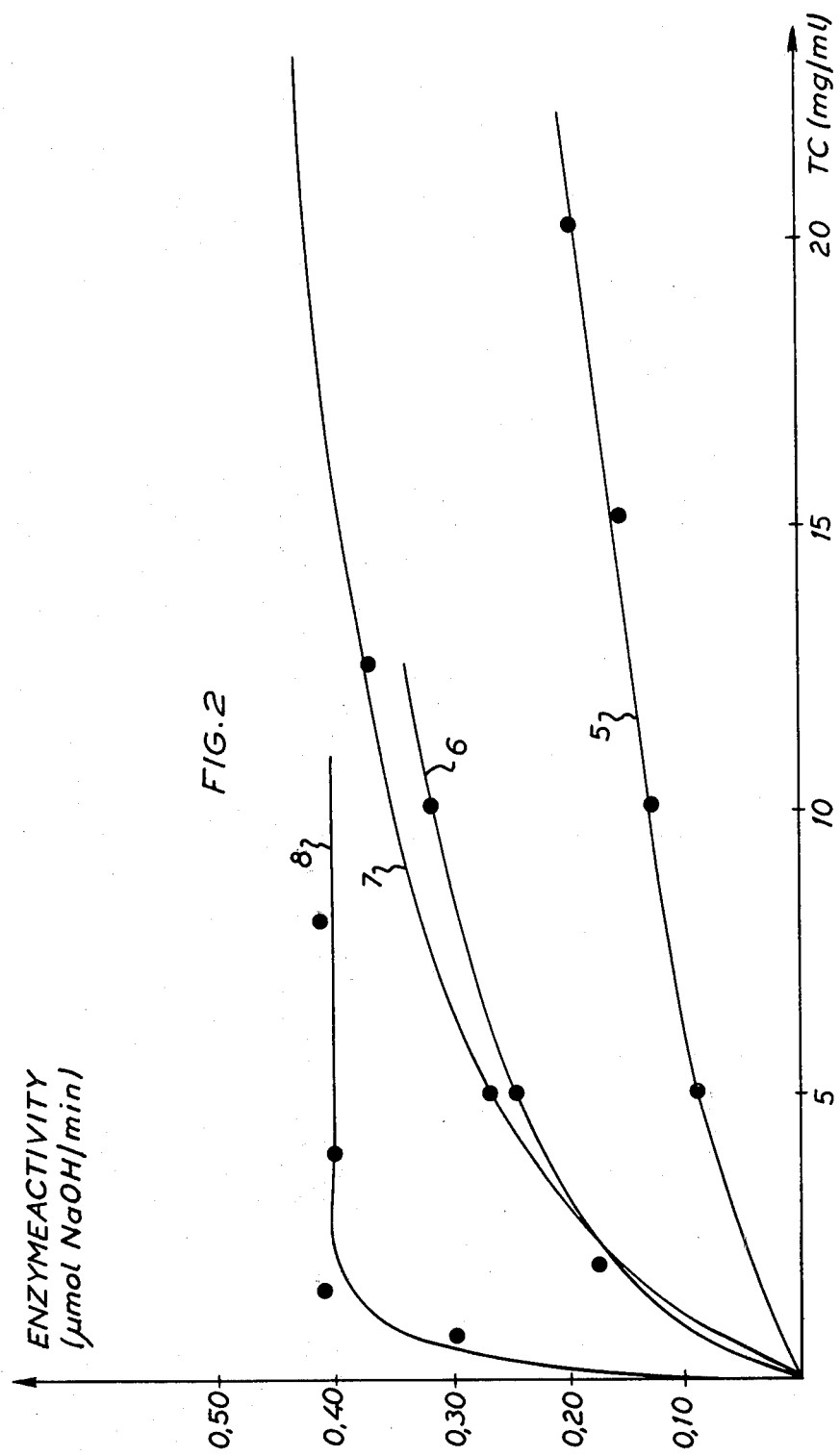

In this example, the substrate composition of Example 2 was compared, on the one hand, with TC coated on Fluosil ® 200 (which is a pyrogenic silica having a surface area of about 200 g/m², from Nynäs Petroleum, Sweden), and on the other, with free emulsified TC (i.e.

without carrier), by the method of Example 9 at an enzyme concentration of 0.2 μg/ml. Coating of TC on Fluosil ® 200 was performed in accordance with the method of Example 1. Two coatings with TC on Fluosil ® 200 were effected, one at 20% by weight of TC and the other at 50% by weight of TC. The results of the measurements with the above-mentioned preparations of carrier-bound substrate and emulsion, respectively, appear from Table 7 and FIG. 2.

As appears from Table 7, maximum and constant enzyme activity (substrate saturation) is obtained upon addition of a certain, very small amount of substrate composition consisting of TC coated on PVC according to Example 2.

In the case of the two coatings of Fluosil ® 200 and the emulsion of TC, no such rapid substrate saturation was obtained. Enzyme activity increased with each addition of substrate.

The substrate concentration at which substrate saturation occurs, is dependent upon the enzyme concentration. The higher the enzyme concentration is, the higher substrate concentration is required for obtained substrate saturation.

TABLE 7

| Substrate form | Enzyme activity (μmol NaOH/min) | | | | | | |
|---|---|---|---|---|---|---|---|
| | Amount of substrate (carrier-bound or emulsion) (mg/ml) | | | | | | |
| | 5 | 10 | 15 | 20 | 25 | 50 | 75 |
| Emulsified TC (curve 5) | 0.09 | 0.13 | 0.16 | 0.20 | — | — | — |
| 20% on Fluosil ® 200 (curve 6) | — | 0.27 | — | — | 0.37 | 0.44 | 0.49 |
| 50% on Fluosil ® 200 (curve 7) | — | 0.18 | — | — | 0.25 | 0.32 | — |
| 16% on PVC acc. to Ex. 2 (curve 8) | 0.30 | 0.41 | — | — | 0.40 | 0.41 | — |

EXAMPLE 15

In this example, the carrier material PVC (PE 712, Kema Nord) was compared with the following carrier materials: Polymethylmethacrylate (FP 4000 Bofors Nobel Kemi, Karlskoga, Sweden), Polyacrylonitrile (Lonza, Switzerland), HD-polyethylene (Unifoss, Stenungsund, Sweden).

Coating was effected according to the method of Example 1. The substrate properties were tested according to the method of Example 9 at an enzyme concentration of 1.0 μg/ml. The result of these tests appears from Table 8.

TABLE 8

| Amount of carrier-bound substrate (mg/ml) | Enzyme activity (μmol NaOH/min) | | | |
|---|---|---|---|---|
| | 16% TC on PVC acc. to Ex. 2 | 16% TC on polymethylmethacrylate | 16% TC on polyacrylonitrile | 16% TC on polyethylene |
| 35 | 1.30 | 0.045 | 0.57 | 0.21 |

It will be appreciated from these results that PVC gives the by far highest reaction rate. Polyacrylonitrile and polymethylmethacrylate give irregular activity curves, which indicates deactivation of the enzyme at the substrate surface. Polyethylene displays increasing enzyme activity, which may indicate that tricaproin loosens from the carrier.

Staining of substrate preparations suspended in aqueous solution with the colorant Sudan red insoluble in aqueous solution, gave the following result: The PVC coating was faintly coloured, the polymethylmethacrylate coating was not coloured at all, the polyacrylonitrile coating was faintly coloured and the polyethylene coating was strongly coloured. The strong staining of the polyethylene coating indicates that there is a large amount of free tricaproin on the surface of the coating. The weak staining of PVC and polyacrylonitrile indicates that there is a lesser amount of free tricaproin on the surface, while the absence of colouring of the polymethylmethacrylate indicates the absence of free tricaproin on the surface. The results of staining with Sudan red correspond well to the results of the enzyme activity determinations.

We claim:

1. A pulverulent enzymatic substrate composition which composition comprises a water-insoluble hydrophobic enzymatic substrate adsorbed on a particulate polyvinyl chloride free of plasticizer and wherein the polyvinyl chloride has an average grain size of at most 0.5 mm, said substrate making up 1-30% by weight of the composition.

2. A substrate composition as claimed in claim 1, characterized in that the substrate makes up 5-25% by weight of the composition.

3. A substrate composition as claimed in claim 1, characterized in that the carrier grains consist of agglomerates of primary particles of an average particle size of 0.1-1 μm.

4. A substrate composition as claimed in claim 1, characterized in that the carrier consists of polyvinyl chloride prepared by emulsion polymerization.

5. A substrate composition as claimed in claim 1, characterized in that the substrate is selected from liquid and solid triglycerides.

6. A substrate composition as claimed in claim 5, characterized in that the substrate is glyceryltricapronate.

7. An aqueous suspension for use in an enzymatic reaction, said suspension comprising (a) a water phase, and (b) the pulverulent substrate composition of claim 1 suspended in said water phase.

8. An enzymatic time-temperature-integrating device comprising two compartments separated by a rupturable partition, wherein one compartment contains the aqueous suspension of claim 7, and the other compartment contains an enzyme for said substrate, and at least one of the compartments includes a pH indicator.

9. An enzymatic time-temperature-integrating device comprising a compartment which contains an aqueous solution including an enzyme and a pH indicator, said aqueous solution having suspended therein the pulverulent substrate composition of claim 1.

10. A method of enzymatic reaction comprising providing an aqueous solution including an enzyme and a pH indicator, combining said aqueous solution with a composition comprising the pulverulent substrate composition of claim 1, reacting said enzyme with said substrate, and determining a change in colour of said solution caused by a change of pH.

11. A method of determining the activity of an enzyme, comprising providing an aqueous solution including the enzyme and adding to said solution a predetermined amount of the pulverulent substrate composition of claim 1, reacting the enzyme with the substrate while generating an enzymatic reaction product, the determination of enzymatic activity being based on the amount of reaction product produced per time unit.

12. A method of determining the activity of an enzyme, comprising providing an aqueous solution including the enzyme and adding to said solution a predetermined amount of the pulverulent substrate composition of claim 1, agitating said mixture and maintaining the pH of said mixture constant by the addition of a base or an acid, and determining the activity of the enzyme as the added amount per time unit of said base or acid.

13. A substrate composition as claimed in claim 1, wherein the composition additionally includes tenside.

14. A substrate composition as claimed in claim 13, characterized in that it comprises 0.1–3% by weight of tenside.

15. A substrate composition as claimed in claim 3, characterized in that the composition contains 1–2% by weight of tenside.

* * * * *